United States Patent [19]

Kapur et al.

[11] Patent Number: 4,554,104

[45] Date of Patent: Nov. 19, 1985

[54] DEHALOGENATION PROCESS OF A PENICILLANIC ACID DERIVATIVE

[75] Inventors: Jagdish C. Kapur; Herman P. Fasel, both of Delft, Netherlands

[73] Assignee: Gist-Brocades N.V., Delft, Netherlands

[21] Appl. No.: 659,088

[22] Filed: Oct. 10, 1984

[30] Foreign Application Priority Data

Oct. 18, 1983 [EP] European Pat. Off. ........ 83201500.2

[51] Int. Cl.$^4$ .................. C07D 499/00; A61K 31/425
[52] U.S. Cl. ...................... 260/245.2 R; 260/245.2 T; 514/192
[58] Field of Search ................. 260/245.2 R, 245.2 T; 424/270; 514/192

[56] References Cited

U.S. PATENT DOCUMENTS 4,419,284  12/1983  Crawford et al. ........... 260/245.2 R

*Primary Examiner*—N. S. Rizzo
*Attorney, Agent, or Firm*—Bierman, Peroff & Muserlian

[57] ABSTRACT

A novel process for the preparation of high purity penicillanic acid-1,1-dioxide comprising subjecting 6,6-dibromo-penicillanic acid-1,1-dioxide to dehalogenation with magnesium in association with an acid in high yields.

9 Claims, No Drawings

DEHALOGENATION PROCESS OF A PENICILLANIC ACID DERIVATIVE

STATE OF THE ART

The presumed association between the resistance of certain bacteria to β-lactam antibiotics and the capability of these bacteria to produce and secrete β-lactamases has led to an intensive search for β-lactamase inhibitors. Dutch patent application No. 7806126 states that penicillanic acid-1,1-dioxide and salts and esters thereof have useful pharmacological properties, for example as effective inhibitors of several types of β-lactamases present in various kinds of bacteria. In the said Dutch application, a process is described for the preparation of penicillanic acid-1,1-dioxide and salts and esters thereof by oxidation of penicillanic acid.

Another process for the preparation of penicillanic acid-1,1-dioxide is described in Dutch patent application No. 8001285 wherein penicillanic acid-1,1-dioxide is prepared by diazotisation-bromination of 6-aminopenicillanic acid followed by oxidation of the formed 6,6-dibromo-penicillanic acid into 6,6-dibromo-penicillanic acid-1,1-dioxide and dehalogenation of the latter compound.

The preferred dehalogenation reaction of 6,6-dibromo-penicillanic acid-1,1-dioxide described in the said application is reduction with hydrogen in the presence of a palladium catalyst but this process has the disadvantages that it uses the highly flammable and explosive hydrogen gas and that special equipment has to be used to carry out the reaction under a pressure of 2 to 5 atmosphere. Two other dehalogenation methods are described in the said application but these reactions, i.e. reduction with zinc in a phosphate buffer or in acetic acid and reduction with tributyl tin hydride give low yields of often impure product.

OBJECTS OF THE INVENTION

It is an object of the invention to provide an improved process for reduction of 6,6-dibromo-penicillanic acid-1,1-dioxide while avoiding the disadvantages of the prior art.

This and other objects and advantages of the invention will become obvious from the following detailed description.

THE INVENTION

The novel process of the invention for the preparation of penicillanic acid-1,1-dioxide comprises subjecting 6,6-dibromo-penicillanic acid-1,1-dioxide to dehalogenation with magnesium in association with an acid. Penicillanic acid-1,1-dioxide of high purity is prepared in an excellent yield by this process. The use of magnesium metal as an excellent dehalogenation reagent under mild conditions is hitherto unknown in the literature. This result is even more surprisingly because experiments to reduce in the same way esters of 6,6-dibromo-penicillanic acid, for instance the methyl and pivaloyl ester, did not succeed.

When using the process of the present invention, it is possible to prepare penicillanic acid-1,1-dioxide in a yield of 90% and in comparison with the process described in the Dutch patent application No. 8001285, a relative improvement of the yield of penicillanic acid-1,1-dioxide of 50% is reached. Furthermore, it is not necessary to use the highly flammable and explosive hydrogen gas, and the reaction can be performed in the usual equipment without any additional requirements to carry out the reaction under high pressure.

It is another advantage of the invention that penicillanic acid-1,1-dioxide of very high purity is obtained, thus avoiding an additional purification procedure. The purity of the product which is isolated directly from the reaction mixture amounts to at least 95% and this product is contaminated with less than 5 ppm of magnesium. In this respect, a product prepared by reduction with hydrogen in association with a palladium catalyst very often is contaminated with a comparatively high amount of palladium. Furthermore, the product has a white color which is important for substances to be used for the preparation of pharmaceutical products.

In European patent application No. 83200542 which is not prepublished, a process is described for dehalogenation of 6α-bromo-penicillanic acid-1,1-dioxide and 6,6-dibromo-penicillanic acid-1,1-dioxide by reduction with zinc in association with an acid having a pKa-value measured in water of less than 3.5 in a water-containing medium. The present invention also shows improvements with respect to this process with the most important improvement of the new method of reduction with magnesium being that the product is completely colorless, while in the case of reduction with zinc, the product always has a yellow color, sometimes even a light brown color. This is especially important when the compound is used for the preparation of pharmaceutical preparation, for which it is always very important to contain as little contaminants, especially colored contaminants, as possible.

Other improvements are the slightly higher yields, the fact that the reaction can be performed at a somewhat lower temperature at the same time, and that the price of magnesium is lower than the price of the equivalent amount of zinc. Furthermore, the magnesium salts which are formed as by products of the new process will form a smaller contamination load for the environment than the zinc salts formed in the other process.

Examples of acids which can be used in the present invention are hydrochloric acid, hydrobromic acid, sulfuric acid, boric acid, perchloric acid, aryl sulfonic acids such as p-tolyl-sulfonic acid and sufficiently acidic alkanoic acids and alkanoic diacids. Preferably hydrochloric acid, hydrobromic acid and sulfuric acid are used, more preferably hydrochloric acid.

The reaction is carried out at a pH of 2.5 to 7, preferably 4 to 6 and is carried out in a mixture of a water-miscible or partly water-miscible inert organic solvent and water. Suitable organic solvents are ethyl acetate, butyl acetate and acetonitrile. Preferably ethyl acetate is used. The reaction is carried out at a temperature between $-10°$ and $25°$ C., preferably between $-3°$ and $10°$ C. Preferably magnesium powder is used in the reaction.

In the following examples there are described several preferred embodiments to illustrate the invention. However, it is to be understood that the invention is not intended to be limited to the specific embodiments.

The purity of 6,6-dihalo- or 6α-halopenicillanic acid-1,1-dioxide was determined through its 60 MHz NMR spectrum in acetone-$d_6$ using 2,6-dichloroacetophenone as the reference and the purity of penicillanic acid-1,1-dioxide (PAS) was determined through HPLC analysis using a standard preparation whose purity has been established through its 360 MHZ NMR spectrum in acetone-$d_6$ with 2,6-dichloroacetophenone as the reference. Magnesium metal powder used in the present invention was purchased from Riedel-De Haën AG.

EXAMPLE 1

To a well-stirred solution of 6.0 g (purity by 60 MHz NMR spectrum in acetone-$d_6$ using 2,6-dichloroacetophenone as the reference: 97.35%; 14.9 mmol) of 6,6-dibromo-penicillanic acid-1,1-dioxide in 150 ml of ethyl acetate and 35 ml of water kept at $-2°$ to $3°$ C. was added portionwise 3.8 g of magnesium powder, while maintaining the pH of the reaction at 3.5 with 4N hydrochloric acid. The contents were stirred for another 2 hours while maintaining the pH at 3.5 with 4N hydrochloric acid and the temperature at $-2°$ to $3°$ C. Then, the solid was filtered, washed with water and ethyl acetate and the combined filtrate was adjusted to a pH of 2.0 with 4N hydrochloric acid whereupon the layers were separated. The aqueous layer was extracted 3 times with 80 ml of ethyl acetate, after which the combined extracts were washed with brine ($2 \times 60$ ml), dried over anhydrous magnesium sulfate and filtered. The filtrate was evaporated to dryness under reduced pressure to obtain a white solid product which was taken up in n-hexane. The solution was filtered and the filtrate was evaporated to dryness under reduced pressure to obtain 3.125 g of penicillanic acid-1,1-dioxide with a purity by 360 MHz spectrum of 96.3% giving a yield of 87%.

EXAMPLE 2

The reaction was carried out as described in Example 1 using 6.0 g (purity by NMR 95.85%; 14.7 mmol) of 6,6-dibromo-penicillanic acid-1,1-dioxide and 4.6 g of powdered magnesium at pH=2 (maintained with 4N HCl) and a reaction time of 5 hours. The isolated yield of penicillanic acid-1,1-dioxide was 3.092 g with a purity by HPLC of 75% given a yield of 68%.

EXAMPLE 3

The reaction was carried out as described in Example 1 using 6.0 g (purity by NMR=95.7%; 14.9 mmol) of 6,6-dibromo-penicillanic acid-1,1-dioxide and 2.44 g of powdered magnesium at pH=4 (maintained with 4N HCl) and a reaction time of 4 hours. The isolated yield of penicillanic acid-1,1-dioxide was 3.117 g with a purity by HPLC of 96% giving a yield of 87%.

EXAMPLE 4

The reaction was carried out as described in Example 1 using 6.0 g (purity by NMR=98.6%; 15.13 mmol) of 6,6-dibromo-penicillanic acid-1,1-dioxide and 2.13 g of powdered magnesium at pH=5 (maintained with 4N HCl) and a reaction time of 3.5 hours. The isolated yield of penicillanic acid-1,1-dioxide was 3.221 g with a purity by HPLC of 95% given a yield of 87%.

EXAMPLE 5

The reaction was carried out as described in Example 1 using 6.0 g (purity by NMR=96.5%; 14.8 mmol) of 6,6-dibromo-penicillanic acid-1,1-dioxide and 2.34 g of powdered magnesium at pH=6 (maintained with 4N HCl) and a reaction time of 4.16 hours. The isolated yield of penicillanic acid-1,1-dioxide was 3.112 g with a purity by HPLC of 96% giving of 87%.

EXAMPLE 6

The reaction was carried out as described in Example 1 using 6.0 g (purity by NMR=96%; 14.7 mmol) of 6,6-dibromo-penicillanic acid-1,1-dioxide and 2.5 g of powdered magnesium at a temperature of 5° to 10° C. and a reaction time of 2.5 hours. The isolated yield of penicillanic acid-1,1-dioxide was 3.045 g with a purity by HPLC of 94% giving a yield of 83%.

EXAMPLE 7

The reaction was carried out as described in Example 1 using 6.0 g (purity of NMR=96%; 14.7 mmol) of 6,6-dibromo-penicillanic acid-1,1-dioxide and 2.44 g of powdered magnesium at a temperature of 22° and a reaction time of 2.45 hours. The isolated yield of penicillanic acid-1,1-dioxide was 2.894 g with a purity by HPLC of 95.5% giving a yield of 80%.

EXAMPLE 8

The reaction was carried out as described in Example 1 using 6.0 g (purity of NMR=96%; 14.7 mmol) of 6,6-dibromo-penicillanic acid-1,1-dioxide and 2.01 g of powdered magnesium in butylacetate instead of ethyl acetate and a reaction time of 2 hours. The isolated yield of penicillanic acid-1,1-dioxide was 3.091 g with a purity by HPLC of 95.5% giving a yield of 86%.

EXAMPLE 9

The reaction was carried out as described in Example 1 using 6.0 g (purity by NMR=96%; 14.7 mmol) of 6,6-dibromo-penicillanic acid-1,1-dioxide and 4.3 g of powdered magnesium in methyl acetate instead of ethyl acetate and a reaction time of 7.4 hours. The isolated yield of penicillanic acid-1,1-dioxide was 2.545 g with a purity by HPLC of 94% giving a yield of 70%.

EXAMPLE 10

The reaction was carried out as described in Example 1 using 6.09 g (purity by NMR=95.6%; 14.7 mmol) of 6,6-dibromo-penicillanic acid-1,1-dioxide and 3.8 g of powdered magnesium in acetonitrile instead of ethyl acetate and a reaction time of 4 hours. The isolated yield of penicillanic acid-1,1-dioxide was 2.792 g with a purity by HPLC of 92% giving a yield of 75%.

EXAMPLE 11

The reaction was carried out as described in Example 1 using 6.0 g (purity by NMR=96.25%; 14.8 mmol) of 6,6-dibromo-penicillanic acid-1,1-dioxide and 4.55 g of powdered magnesium and 4N.$H_2SO_4$ instead of 4N HCl and a reaction time of 12 hours. The isolated yield of penicillanic acid-1,1-dioxide was 2.985 g with a purity by HPLC of 69.5% giving a yield of 60%.

EXAMPLE 12

The reaction was carried out as described in Example 1 using 6.0 g (purity by NMR=95.1%; 14.6 mmol) of 6,6-dibromo-penicillanic acid-1,1-dioxide and 2.7 g of powdered magnesium and 4N HBr instead of 4N HCl and a reaction time of 4 hours. The isolated yield of penicillanic acid-1,1-dioxide was 3.034 g with a purity by HPLC of 94% giving a yield of 84%.

EXAMPLE 13

The reaction was carried out as described in Example 1 using 6.0 g (purity of NMR=94.65%; 14.5 mmol) of 6,6-dibromo-penicillanic acid-1,1-dioxide and 2.48 g of powdered magnesium and 4N $HClO_4$ instead of 4N HCl and a reaction time of 4 hours. The isolated yield of penicillanic acid 1,1-dioxide was 2.44 g with a purity by HPLC of 93% giving a yield of 67%.

EXAMPLE 14

The reaction was carried out as described in Example 1 using 6.0 g (purity of NMR=96%; 14.7 mmol) of 6,6-dibromo-penicillain acid-1,1-dioxide and 3.8 g of magnesium and solid boric acid instead of 4N HCl and a pH of 7 instead 3.5 and a reaction time of 4 hours. The isolated yield of penicillanic acid-1,1-dioxide was 2.256 g with a purity by HPLC of 93% giving a yield of 65.7%.

EXAMPLE 15

The reaction was carried out as described in Example 1 however, using 3.0 g (purity by MNR=96%; 9.2 mmol) of 6α-bromo-penicillanic acid instead of 6,6-dibromo-penicillanic acid-1,1-dioxide and 1.9 g powdered magnesium and a reaction time of 4 hours. The isolated yield of penicillanic acid-1,1-dioxide was 1.897 g with a purity by HPLC of 100% giving a yield of 89%.

Various modifications of the process of the invention may be made without departing from the spirit or scope thereof and it should be understood that the invention is intended to be limited only as defined in the appended claims.

What we claim is:

1. A process for the preparation of penicillanic acid-1,1-dioxide comprising subjecting 6,6-dibromo-penicillanic acid-1,1-dioxide to dehalogenation with magnesium in association with an acid.

2. The process of claim 1 wherein the acid is selected from the group consisting of hydrochloric acid, hydrobromic acid and sulfuric acid.

3. The process of claim 1 wherein the acid is hydrochloric acid.

4. The process of claim 1 wherein the pH at which the debromination is effected is 2.5 to 7.

5. The process of claim 4 wherein the pH is 4 to 6.

6. The process of claim 1 wherein the reaction is performed at a temperature between $-5°$ and $20°$ C.

7. The process of claim 1 wherein the reaction temperature is between $-3°$ and $10°$ C.

8. The process of claim 1 wherein the reaction is carried out in a mixture of water-miscible or partly water-miscible, inert organic solvent and water.

9. The process of claim 8 wherein the reaction is carried out in ethyl acetate and water.

* * * * *